United States Patent [19]
Pan

[11] Patent Number: 6,115,446
[45] Date of Patent: Sep. 5, 2000

[54] FAST RECONSTRUCTION OF FAN-BEAM CT AND SPECT

[75] Inventor: Xiao Chuan Pan, Chicago, Ill.

[73] Assignee: Arch Development Corp., Chicago, Ill.

[21] Appl. No.: 09/289,297

[22] Filed: Apr. 9, 1999

[51] Int. Cl.[7] .................................................. A61B 6/03
[52] U.S. Cl. ................................. 378/4; 378/19; 378/99
[58] Field of Search .............................. 378/4, 8, 15, 94; 382/131

[56] References Cited

U.S. PATENT DOCUMENTS

| | | | |
|---|---|---|---|
| 5,406,479 | 4/1995 | Harman | 378/7 |
| 5,446,799 | 8/1995 | Tuy | 382/132 |
| 5,946,371 | 8/1999 | Lai | 378/19 |

OTHER PUBLICATIONS

Arenson, Jerry, *Data Collection Strategies: Gantries and Detectors*, (Hackensack, New Jersey: Elscint Inc., [no date]).

Barrett, Harrison H., *The Radon Transform and its Applications*, Progress in Optics XXI:218–286 (Elsevier Science Publishers B.V., 1984).

Budinger, Thomas F., *Single Photon Emission Computed Tomography*, ([no date]).

Defrise, Michel, et al., *Exact and Approximate Rebinning Algorithms for 3–D PET Data*, 16:2 IEEE Transactions on Medical Imaging 145–158 (Apr. 1997).

Dreike, Philip, et al., *Convolution Reconstruction of Fan Beam Projections*, 5 Computer Graphics and Image Processing 459–469 (Academic Press, Inc., 1976).

Gullberg, Grant T., et al., *Reconstruction Algorithm for Fan Beam with a Displaced Center–of–Rotation*, MI–5:1 IEEE Transactions on Medical Imaging 23–29 (Mar. 1986).

Gullberg, Grant T., *The Reconstruction of Fan–Beam Data by Filtering the Back–Projection* 10 Computer Graphics and Image Processing 30–47 (1979).

Horn, Berthold K. P., *Fan–Beam Reconstruction Methods*, 67:12 Proceedings of the IEEE 1616–1623 (Dec. 1979).

Jerri, Abdul J., *The Shannon Sampling Theorem–Its Various Extensions and Applications: A Tutorial Review*, 65:11 Proceedings of the IEEE 1565–1596 (Nov. 1977).

Joseph, Peter M., *Overview of the History and Principles of CT Scanning* (University of Pennsylvania, Dept. of Radiology, [no date]).

Kalender, Willi A., et al., *Spiral CT: Medical Use and Potential Industrial Applications*, 3149 Proceedings of SPIE 188–202 (Jul. 1997).

Kijewski, Marie Foley, et al., *The noise power spectrum of CT images*, 32:5 Phys.Med.Biol. 565–575 (1987).

Metz, Charles E., et al., *A Unifed Analysis of Exact Methods of Inverging the 2–D Exponential Radon Transform, with Implications for Noise Control in SPECT*, 14:4 IEEE Transactions on Medical Imaging 643–658 (1995).

Meyer, Craig H., et al., *Fast Spiral Coronary Artery Imaging*, 28 Magnetic Resonance in Medicine 202–213 (1992).

(List continued on next page.)

Primary Examiner—David V. Bruce
Attorney, Agent, or Firm—Welsh & Katz, Ltd.

[57] ABSTRACT

A method and apparatus for reconstructing a tomographic image using the parallel beam filtered backprojection algorithm from fan beam data, $q(\alpha, \beta)$. The method includes the steps of performing a fast fourier transform on the fan beam data, $q(\alpha, \beta)$, with respect to a set of projection angles, $\beta$ and forming a linear combination of complementary data elements of the transformed data, lying at projection bins of $\alpha$ and $-\alpha$. The method further includes the steps of linearly interpolating the linear combination to obtain a regularly spaced set of data, $P_k^{(\infty)}(\xi)$, in fourier space and performing an inverse fourier transform on the linearly interpolated data. Finally, the method includes the step of reconstructing an image from the inverse transformed data using the filtered back projection algorithm.

21 Claims, 4 Drawing Sheets-

OTHER PUBLICATIONS

Mueller, Rolf K., et al., *Reconstructive Tomography and Applications to Ultrasonics*, 67:4 Proceedings of the IEEE 567–586 (Apr. 1979).

Parker, Dennis L., *Optimal short scan convolution reconstruction for fanbeam CT*, 9:2 Med.Phys. 254–257 (Mar./Apr. 1982).

Riederer, Stephen J., et al., *The Noise Power Spectrum in Computed X–ray Tomography*, 23:3 Phys.Med.Biol. 446–454 (1978).

Vannier, M.W., et al., *Principles of Spiral CT*, ([no date]).

You, Hangsheng, et al., *Benefits of Angular Expression to Reconstruction Algorithms for Collimators with Spatially Varying Focal Lenghts*, 16:5 IEEE Transactions on Medical Imaging 527–531 (Oct. 1997).

FAST RECONSTRUCTION OF FAN-BEAM CT AND SPECT

FIELD OF THE INVENTION

The invention relates to the field of image processing and more particularly to tomographic imaging.

BACKGROUND OF THE INVENTION

In tomographic imaging, a finite set of imaging samples are obtained of the underlying multi-dimensional function of interest. However, because of various physical restrictions of the sampling system, these samples are often obtained on nonuniform grids, thereby preventing the direct use and meaningful interpretation of these data. For example, in medical tomographic imaging such as the two-dimensional (2D) fan-beam computed tomography (CT), single-photon emission computed tomography (SPECT), positron emission tomography (PET), spiral (or helical) CT, diffraction tomography (DT), and magnetic resonance imaging (MRI), the acquired data are often sampled on nonuniform grids in the sinogram space, thus preventing the direct use of existing methods that are computationally efficient and numerically stable for reconstruction of tomographic images. In these situations, one can always use various multi-dimensional interpolation (MDI) methods to convert the samples that lie on nonuniform grids into samples that lie on uniform grids so that they can be processed directly and be presented meaningfully.

A wide variety of MDI methods have previously been developed. The methods that are based upon the Whittaker-Shannon sampling (WST) theorem can potentially provide accurate interpolation results. Unfortunately, these methods generally possesses the shortcoming of great computational burden, which increases drastically as the number of interpolation dimensions increases ("the curse of the dimensionality"). Attempts have been made to alleviate the computational burden by developing efficient interpolation methods. However, these methods are all associated with certain approximations. Virtually all of the previously developed methods calculate the desired uniform samples directly from the measured nonuniform samples, which generally requires the use of computationally burdensome algorithms if accuracy is to be preserved.

SUMMARY

A method and apparatus are provided for reconstructing a tomographic image using the filtered backprojection algorithm from fan beam data, $q(\alpha,\beta)$. The method includes the steps of performing a fast fourier transform on the fan beam data, $q(\alpha,\beta)$, with respect to the projection angle, $\beta$ and forming a linear combination of complementary data elements of the transformed data, lying at projection bins of $+\alpha$ and $-\alpha$. The method further includes the steps of linearly interpolating the linear combination to obtain a regularly spaced set of data, $P_k^{(w)}(\xi)$, in fourier space and performing an inverse fourier transform on the linearly interpolated data. Finally, the method includes the step of reconstructing an image from the inverse transformed data using the filtered back projection algorithm.

DETAILED DESCRIPTION OF A PREFERRED EMBODIMENT

Figure 1:
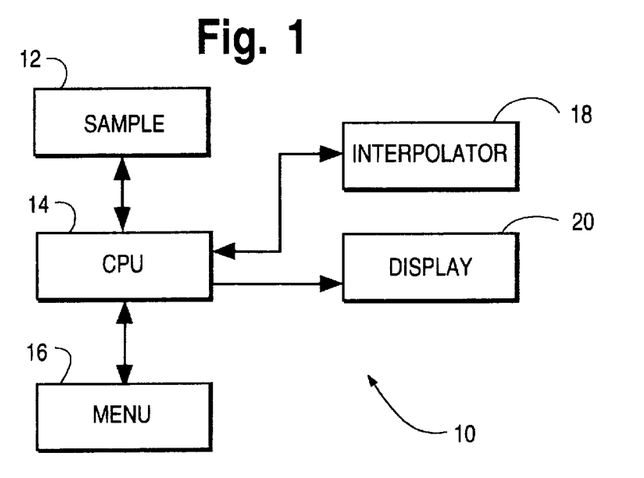
FIG. 1 is a block diagram of an imaging system using the multidimensional interpolation system in accordance with an embodiment of the invention.
Figure 2:
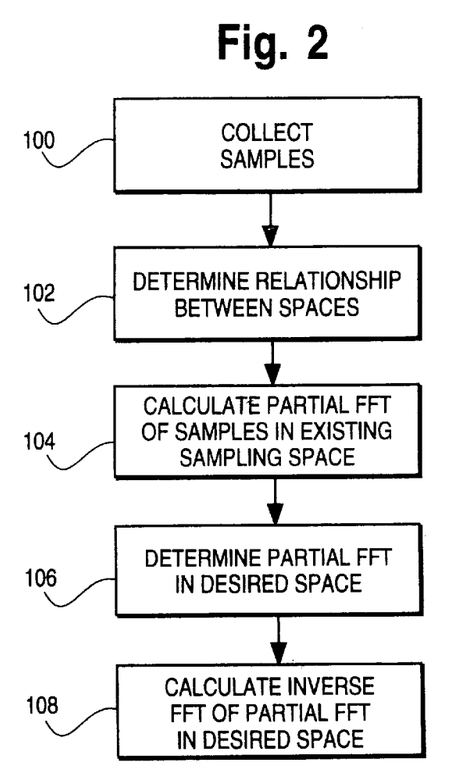
FIG. 2 is a flow chart of the interpolation method of the system of FIG. 1.

FIG. 1 is a multidimensional interpolator 10, generally, in accordance with an illustrated embodiment of the invention. FIG. 2 is a flow chart of processing steps that may be used by the structure of FIG. 1 to interpolate between sampling spaces. Reference may be made to FIGS. 1 and 2 as appropriate to an understanding of the invention.

Under the embodiment, a sampling device 12 acquires samples 100 under an appropriate format (e.g., fan-beam CT, spiral CT, etc.) under the control of a central processing unit (CPU) 14. The CPU 14 may store the samples in a memory unit 16 or processing the samples directly.

Once collected, the samples may be transferred to an interpolator 18. Within the interpolator 18, the samples may be interpolated from a second sampling format (e.g., fan-beam CT) into a first sampling format (e.g., parallel ray CT) under the control of the CPU 14. Once converted the samples may be displayed under a conventional format on a display 20.

In general, conventional interpolation techniques calculate a function by directly using its measured samples. However, because the values of a function can readily be calculated from its Fourier transform (FT), the interpolation task could be compared to estimating the FT of a function from its measured samples. Based upon this observation, an approach is provided for reducing the interpolation dimensions in MDI problems.

Let $f(\vec{x}_1, \vec{x}_2)$ and $g(\vec{y}_1, \vec{y}_2)$ be K-dimensional (KD) band-limited functions, where $\vec{x}_1=(x_1,x_2 \ldots x_k)^T$ and $\vec{y}_1=(y_1,y_2 \ldots y_k)^T$ are kD vectors, $\vec{x}_2=(x_{k+1},x_{k+2} \ldots x_K)^T$ and $\vec{y}_2=(y_{k+1},y_{k+2} \ldots y_K)^T$ are MD vectors, and K=M+k and K>k. Suppose that $f(\vec{x}_1, \vec{x}_2)=g(\vec{y}_1, \vec{y}_2)$ mathematically. Because the transformation between the $\{\vec{x}_1, \vec{x}_2\}$ and $\{\vec{y}_1, \vec{y}_2\}$ spaces can be generally non-linear, uniform samples of $g(\vec{y}_1, \vec{y}_2)$ in the $\{\vec{y}_1, \vec{y}_2\}$ space produce generally nonuniform samples of $f(\vec{x}_1, \vec{x}_2)$ in the $\{\vec{x}_1, \vec{x}_2\}$ space. The MDI task is to estimate uniform samples of $f(\vec{x}_1,$ $\vec{x}_2$) in the $\{\vec{x}_1, \vec{x}_2\}$ space from a set of measured uniform samples of $g(\vec{y}_1, \vec{y}_2)$ in the $\{\vec{y}_1, \vec{y}_2\}$ space, where the sampling rate satisfies the Nyquist conditions. In a wide class of MDI problems such as those that arise in medical imaging, the transformation between the $\{\vec{x}_1, \vec{x}_2\}$ and $\{\vec{y}_1, \vec{y}_2\}$ spaces has a general form, given by $$\vec{x}_1 = \vec{h}_1(\vec{y}_1) \tag{1a}$$

$$\vec{x}_2 = \vec{h}_2(\vec{y}_1, \vec{y}_2) = a\vec{y}_2 + \vec{b}(\vec{y}_1), \tag{1b}$$

where $\vec{h}_2$ denotes a general linear transformation (LT) between the $\{\vec{x}_2\}$ and $\{\vec{y}_2\}$ subspaces, whereas $\vec{h}_1$ denotes a general non-LT between the $\{\vec{x}_1\}$ and $\{\vec{y}_1\}$ subspaces. The known matrix a is independent of $\vec{y}_1$ and $\vec{y}_2$, and the known vector $\vec{b}$ can be any real or complex function of $\vec{y}_1$. The known matrix a and vector $\vec{b}$ represent transfer functions (i.e., a set of relationships) which relate the first set of samples $f(\vec{x}_1, \vec{x}_2)$ to the second set of samples $g(\vec{y}_1, \vec{y}_2)$ (i.e., the two sampling spaces) in a known manner.

Let $F(\vec{x}_1, \vec{v}_{\vec{x}_2})$ and $G(\vec{y}_1, \vec{v}_{\vec{y}_2})$ be the partial FTs of $f(\vec{x}_1, \vec{x}_2)$ and $g(\vec{y}_1, \vec{y}_2)$ with respect to $\vec{x}_2$ and $\vec{y}_2$, respectively, where $\vec{v}_{\vec{x}_2}$ and $\vec{v}_{\vec{y}_2}$ denote the corresponding frequencies of $\vec{x}_2$ and $\vec{y}_2$. It can be shown that $$F(\vec{x}_1, \vec{v}_{\vec{x}_2}) = \|a\| G(\vec{y}_1, a^T \vec{v}_{\vec{x}_2}) e^{-j2\pi \vec{v}_{\vec{x}_2} \cdot \vec{b}(\vec{y}_1)}, \tag{2}$$

where $\|a\|$ and $a^T$ are the determinant and transpose of a. Because $G(\vec{y}_1, \vec{v}_{\vec{y}_2})$ can readily be obtained with the fast FT (FFT) 104 from the measured samples of $g(\vec{y}_1, \vec{y}_2)$ in $\{\vec{y}_2\}$ subspace, the CPU 14 can calculate $F(\vec{x}_1, \vec{v}_{\vec{x}_2})$ 106 by using Eqn. (2) and then $f(\vec{x}_1, \vec{x}_2)$ in the $\{\vec{x}_2\}$ subspace by invoking the inverse FFT 108. Therefore, the CPU 14 accomplishes the interpolation task in the $\{\vec{x}_2\}$ subspace and effectively reduces the original KD interpolation task of Eqn. (1) to a kD one between the $\{\vec{x}_1\}$ and $\{\vec{y}_1\}$ subspaces.

For another class of MDI problems, the transformation between the $\{\vec{x}_1\}$ and $\{\vec{y}_1\}$ subspaces is described by Eqn. (1a), whereas the transformation between the $\{\vec{x}_2\}$ and $\{\vec{y}_2\}$ subspaces is given by $$x_{k+i} = c_i y_{k+i} + b_i(\vec{y}_1, y_{k+1}, y_{k+2} \ldots y_{k+i-1}), \tag{3}$$

where $x_{k+i}, y_{k+i}, b_i$ and $c_i$ are the components of $\vec{x}_2, \vec{y}_2, \vec{b}$ and $\vec{c}$, $i=1, 2 \ldots M$. We assume that the vectors $\vec{b}$ and $\vec{c}$ are known. It should be noted that $\vec{b}$ in Eqn. (1b) is completely independent of $\vec{y}_2$, whereas $\vec{b}$ in Eqn. (3) can be a general non-linear function of the components of $\vec{y}_2$. One can show that $F(\vec{x}_1, \vec{v}_{\vec{x}_2})$ can be expressed as $$F(\vec{x}_1, v_{k+1}, v_{k+2} \ldots v_{k+M}) = c_1 e^{-j2\pi v_{k+1} b_1(\vec{y}_1)} \times \int dy_{k+1} e^{-j2\pi c_1 v_{k+1} y_{k+1}} G^{(M-1)}(\vec{y}_1, y_{k+1}, v_{k+2} \ldots v_{k+M}) \tag{4}$$

where $\vec{v}_{\vec{x}_2} = (v_{k+1}, v_{k+2} \ldots v_{k+M})^T$, and $$G^{(i)}(\vec{y}_1, y_{k+1} \ldots y_{k+M-i}, v_{k+M-i+1} \ldots v^{k+M}) = c_{M-i+1} e^{-j2\pi v_{k+M-i+1} b_{M+1-i}(\vec{y}_1, y_{k+1} \ldots y_{k+M-i})} \times \int dy_{k+M-i+1} e^{-j2\pi c_{M-i+1} v_{k+M-i+1} y_{k+M-i+1}} G^{(i-1)}(\vec{y}_1, y_{k+1} \ldots y_{k+M-i} y_{k+M-i+1}, v_{k+M-i+2} \ldots v_{k+M}) \tag{5}$$

with $G^{(0)}(\vec{y}_1, y_{k+1} \ldots y_{k+M}) = g(\vec{y}_1, \vec{y}_2)$ and $i=1, 2 \ldots M-1$. The integrals in Eqns. (4) and (5) denote 1D FTs that can be calculated by invoking the ID FFT. Using Eqns. (4) and (5), the CPU 14 can calculate $F(\vec{x}_1, \vec{v}_{\vec{x}_2})$ from knowledge of $g(\vec{y}_1, \vec{y}_2)$ in the $\{\vec{y}_2\}$ subspace. From $F(\vec{x}_1, \vec{v}_{\vec{x}_2})$, the CPU 14 can obtain $f(\vec{x}_1, \vec{x}_2)$ by invoking the inverse FFT and thus accomplish the interpolation task in the $\{\vec{x}_2\}$ subspace. Therefore, the original KD interpolation task of Eqns. (1a) and (3) is thus reduced effectively to a kD one between the $\{\vec{x}_2\}$ and $\{\vec{y}_1\}$ subspaces.

In fan-beam SPECT, the CPU 14 can measure uniform samples of $q(\alpha, \beta)$ in the $\{\alpha, \beta\}$ space using the sampling device 12. Reconstruction of a SPECT image requires uniform samples of $p(\xi, \phi)$ in the $\{\xi, \phi\}$ space. One can show that $p(\xi, \phi) = q(\alpha, \beta)$, provided $$\xi = \frac{\alpha F(\alpha)}{\sqrt{F^2(\alpha + \alpha^2)}} \tag{6a}$$

$$\phi = \beta + \tan^{-1}(\alpha/F(\alpha)) \tag{6b}$$

where $F(\alpha)$ is the focal length which can be spatially varied because it can be a function of $\alpha$. It appears that a 2D interpolation may be used to calculate uniform samples of $p(\xi, \phi)$ in the $\{\xi, \phi\}$ space from that of $q(\alpha, \beta)$ in the $\{\alpha, \beta\}$ space. However, comparison of Eqns. (6b) and (1b) indicates that $\phi$ is a 1D of $\beta$ with $a=1$ and $b=-\tan^{-1}(\alpha/F(\alpha))$ and that the interpolation between the $\{\phi\}$ and $\{\beta\}$ subspaces can thus be accomplished by using Eqn. (2). Thus the seemingly 2D interpolation task here effectively becomes a 1D interpolation task between the $\xi$ and $\alpha$ subspaces.

In fan-beam CT, one can measure uniform samples of $q(\alpha, \beta)$ in the $\{\alpha, \beta\}$ space. Reconstruction of a CT image requires uniform samples of $p(\xi, \phi)$ in the $\{\xi, \phi\}$ space. It can be shown that $p(\xi, \phi) = q(\alpha, \beta)$, provided $$\xi = F(\alpha) \sin \alpha \tag{7a}$$

$$\phi = \beta + \alpha, \tag{7b}$$

where $F(\alpha)$ can be a function of $\alpha$. However, in practical CT, F is generally a constant. Because the transformation in Eqn. (7) is non-linear, a 2D interpolation may be used to calculate uniform samples of $p(\xi, \phi)$ in the $\{\xi, \phi\}$ space from that of $q(\alpha, \beta)$ in the $\{\alpha, \beta\}$ space. However, comparison of Eqns. (7b) and (1b) indicates that $\phi$ is a 1D LT of $\beta$ with $a=1$ and $b=\delta$. The comparison also suggests that the interpolation between the $\{\phi\}$ and $\{\beta\}$ subspaces can thus be accomplished by using Eqn. (2). Hence, the 2D interpolation task in 2D fan-beam CT is reduced effectively to a 1D interpolation task between the $\{\xi\}$ and $\{\alpha\}$ subspaces.

Figure 3A:
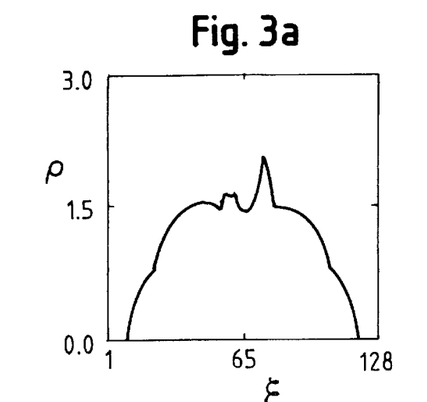
FIGS. 3a and 3b depict results of data interpolated on a 128×128 grid at two different values of $\phi$ by the system of FIG. 1.
Figure 3B:
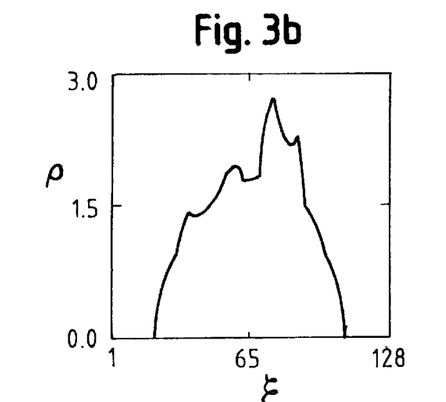
Figure 4A:
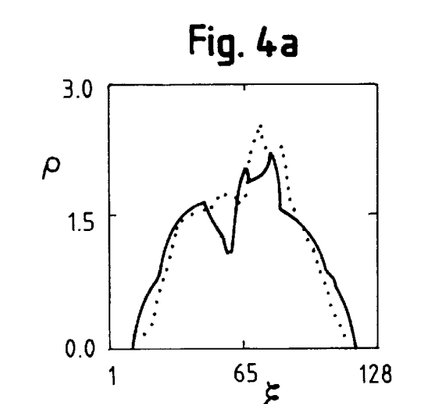
FIGS. 4a and 4b also depict results of data interpolated on a 128×128 grid at two different values of $\phi$ by the system of FIG. 1.
Figure 4B:
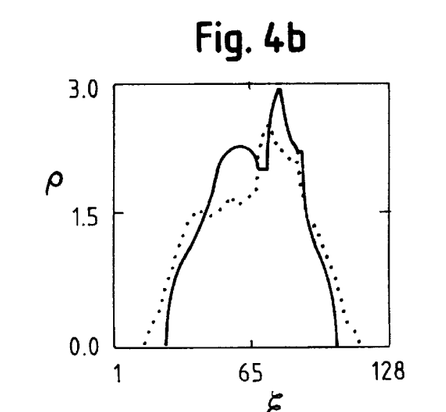

As a further example, two sets of uniform samples of $q(\alpha, \beta)$ were generated on 128×128 and 128×16 grids, respectively, in the $\{\alpha,\beta\}$ space, simulating the measurements in CT. Applying the above-described approach and the frequently used bilinear interpolation (BI) technique, uniform samples of $p(\xi,\phi)$ were calculated in $\{\xi,\phi\}$ from the two sets of the computer-simulated data. The data set used in FIG. 3 contains 128 grids in the $\{\beta\}$ subspace. In this situation, the results obtained with this approach coincide with the true values, suggesting that this approach can generate accurate values of $p(\xi,\phi)$. However, as shown in FIG. 3, despite the fact that the BI technique can yield reasonably accurate results, discrepancies between the BI results and the true values are evident. For the data set that contains only 16 grids in the $\{\beta\}$ subspace, as shown in FIG. 4, the BI technique performs poorly, whereas this approach still yields reasonably accurate results. For the above numerical experiments, this approach is about 3 times faster than the BU technique. Quantitative evaluation indicates that, in terms of root-mean-square error, this approach is generally 5 times more accurate than the BI technique.

In 2D diffraction tomography (DT) with plane incident wave, one can measure uniform samples of $g(v_m,\phi)$ in the $\{v_m,\phi\}$ space. Reconstruction of a DT image requires uniform samples of $f(v_a,\phi_0)$ in the $\{v_a,\phi_0\}$ space. One can show that $f(v_a,\phi_0)=g(v_m,\phi)$, provided $$v_a = \sqrt{v_m^2 + \left(\sqrt{v_0^2 - v_m^2} - v_0^2\right)} \tag{8a}$$

$$\phi_0 = \phi + \tan^{-1}\left(\frac{\sqrt{v_0^2 - v_m^2} - v_0}{v_m}\right), \tag{8b}$$

where $v_0$ is a known constant and $|v_m| \leq v_0$. Because the transformation in Eqn. (8) is non-linear, a 2D interpolation may be used to calculate uniform samples of $f(v_a,\phi_0)$ in the $\{v_a,\phi_0\}$ space from that of $g(v_m,\phi)$ in the $\{v_m,\phi\}$ space. However, comparison of Eqns. (8b) and (1b) indicates that $\phi_0$ is a 1D LT of $\phi$ with a=1 and $$b = \tan^{-1}\left(\frac{\sqrt{v_0^2 - v_m^2} - v_0}{v_m}\right)$$

and that the interpolation between the $\{\phi_0\}$ and $\{\phi\}$ subspaces can thus be accomplished by using Eqn. (2). Hence, the 2D interpolation task in DT is reduced effectively to a 1D interpolation task between the $\{v_a\}$ and $\{v_m\}$ subspaces.

In spiral CT, one can measure uniform samples of $q(\alpha, \beta, z')$ in the $\{\alpha,\beta,z'\}$ space. However, image reconstruction in spiral CT requires uniform samples of $p(\xi,\phi,z)$ in the $\{\xi,\phi,z\}$ space. One can show that $p(\xi,\phi,z)=q(\alpha,\beta,z')$, provided $$\xi = F(\alpha)\sin\alpha \tag{9a}$$

$$\phi = \beta + \alpha \tag{9b}$$

$$z = z' + c(\beta), \tag{9c}$$

where $c(\beta)$ is a known function of $\beta$, and its form depends upon how the scanning is performed in a spiral CT experiment. Because the transformation in Eqn. (9) is obviously non-linear, a 3D interpolation may be used to calculate uniform samples of $p(\xi,\phi,z)$ in the $\{\xi,\phi,z\}$ space from that of $q(\alpha,\beta,z')$ in the $\{\alpha,\beta,z'\}$ space. However, one can show that the transformation between the $\{\phi,z\}$ and $\{\beta,z'\}$ subspaces in Eqns. (9b) and (9c) satisfies Eqn. (3) with $c_1=c_2=1$, $b_1=\alpha$ and $b_2=c(\beta)$. Interpolation between the two subspaces can thus be accomplished by using Eqns. (3) and (4). Therefore, the 3D interpolation task in spiral CT is reduced effectively to a 1D interpolation task between the $\{\xi\}$ and $\{\alpha\}$ subspaces.

The method and apparatus described above can reduce the computational burden by reducing interpolation dimensions in two general classes of MDI problems in Eqns. (1) and (3). This approach is as accurate as the multi-dimensional interpolation techniques that are based upon the WST but is inherently more efficient than the latter because it utilizes the FFT technique. Because the WST interpolation techniques are, in general, more accurate than the linear interpolation (LI) technique, this approach is generally more accurate than the multi-dimensional LI technique. Numerical studies in 2D interpolation problems demonstrate that the proposed approach is more accurate and even (about 3 times) faster than the most commonly used BI technique. The reduction in computation time is expected to be greater as the number of interpolation dimensions increases. Furthermore, this approach can accomplish some interpolation tasks which other interpolation techniques are not applicable to and can not do. The proposed approach can also be applied to other MDI problems such as MRI and PET in medical imaging.

A more detailed example will now be provided. Under the more detailed example, data collected using fan-beam CT will be interpolated into a parallel beam format for faster and more efficient processing.

A linear approach is used that exploits statistically complementary information inherent in the projection data of fan-beam computed tomography (CT) for achieving a bias-free image-variance reduction in fan-beam CT. This linear approach leads to the development of infinite classes of hybrid algorithms for image reconstruction in fan-beam CT. These hybrid algorithms are computationally more efficient and numerically less susceptible to data noise and to the effect of finite sampling than the conventional fan-beam filtered backprojection (FFBP) algorithm. Infinite classes of generalized fan-beam filtered back-projection (GFFBP) algorithms have also been developed, which include the conventional FFBP algorithm as a special member. It is also demonstrated theoretically and quantitatively that the hybrid and GFFBP algorithms are identical (or different) in the absence (or presence) of data noise and of the effect of finite sampling. More importantly, the statistically optimal hybrid algorithm are identified that may have potentially significant implication to image reconstruction in fan-beam CT. Extensive numerical results of computer-simulation studies validated these theoretical results.

Modern CT scanners predominantly employ fan-beam configurations that allow rapid acquisition of projection data. Fan-beam SPECT systems have been developed for improved sensitivity and resolution. Conventional fan-beam filtered backprojection (FFBP) algorithm is widely used for image reconstruction in fan-beam CT and SPECT. The FFBP algorithm is a generalization of the well-known filtered backprojection (FBP) algorithm that reconstructs images from projections obtained with a parellel-beam configuration. However, the FFBP algorithm is computationally less efficient and, as will be shown below, numerically more susceptible to data noise and to the effect of finite sampling than the FBP algorithm.

It is always desirable to enhance the signal-to-noise ratio in CT and SPECT images by optimally reducing image variances without sacrificing the image accuracy and without increasing the radiation dose to the patient. Therefore, it becomes critically important to understand the noise properties in the reconstructed images and to develop statistically optimal reconstruction algorithms in fan-beam CT and SPECT. Although the noise properties of images in parallel-beam CT have been investigated previously, there appears to be a lack of systematic analysis of image noise properties and a lack of investigations of reconstruction algorithms for bias-free image-variance reductions in fan-beam CT and SPECT.

The existence of statistically complementary information inherent in the data of fan-beam CT and SPECT is revealed and a general linear approach that exploits this information is proposed for achieving a bias-free variance reduction in the image. Based upon this linear approach, infinite classes of hybrid algorithms are developed for image reconstruction in fan-beam CT. These algorithms, with little computational load added to that of the FBP algorithm, are computationally more efficient and numerically less susceptible to data noise and to the effect of finite sampling than the conventional FFBP algorithm. Infinite classes of generalized fan-beam filtered backprojection (GFFBP) algorithms are also developed, which include the conventional FFBP algorithm as a special member. It is also shown theoretically that the hybrid and GFFBP algorithms are identical (or different) in the absence (or presence) of data noise and of the effect of finite sampling.

Projections measured with the parallel-beam configuration are herein referred to as ideal sinograms and the projections acquired with a fan-beam configuration are referred to as fan-beam sinograms. An image can be readily reconstructed exactly from its ideal sinogram by using computationally efficient and numerically stable algorithms such as the FBP algorithm. The task of reconstructing an image from the fan-beam sinogram can be characterized as estimating the ideal sinogram from the fan-beam sinogram.

Ideal and fan-beam sinograms and the relationship is well known. There are two types of fan-beam configurations, depending upon whether projections are sampled at equiangular intervals on a curved detector or at equispaced intervals on a flat detector. Here, the focus is on image reconstruction from projections obtained with the equiangular configuration, which is widely used in fan-beam CT. However, the theory developed and the results obtained in this work can readily be extended to the equispaced fan-beam configuration with constant or spatially variant focal length that is widely used in fan-beam SPECT.

Figure 5:
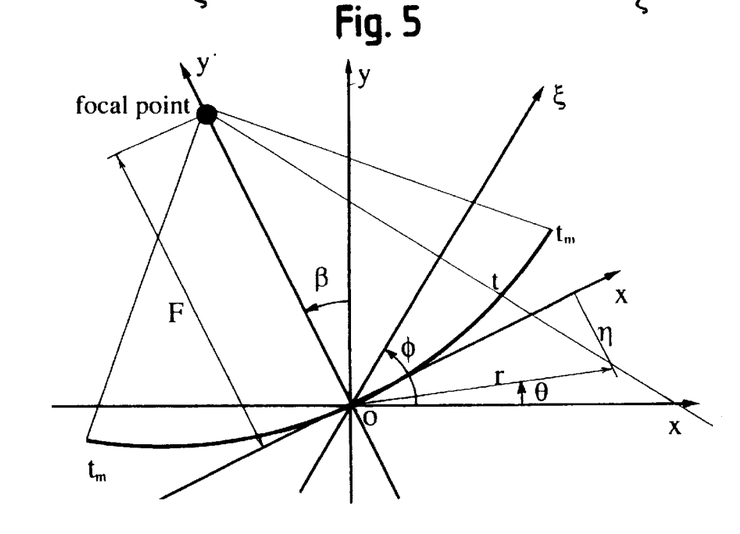
FIG. 5 depicts data gathering angles used by the system of FIG. 1 for interpolating fan-beam data into a parallel beam sampling space.

Let $p(\xi,\phi)$ and $q(\alpha,\beta)$ denote the ideal and fan-beam sinograms, respectively, of an object $a(r,\theta)$, where $\xi$ and $\phi$ (or $\alpha$ and $\beta$) represent the detector-bin index and projection angle in the parallel-beam (or the fan-beam) configuration. It is well-known that, in the absence of noise and of the effect of finite sampling, the two sinograms are mathematically related by $$P(\xi,\phi)=q(\alpha,\beta) \qquad (10)$$

provided that $$\xi=F\sin\alpha \text{ and } \phi=\beta+\alpha, \qquad (11)$$

where F is the distance between the focal point and the center of rotation of the fan-beam system and is referred to as the focal length, as shown in FIG. 5, and $|\alpha|\leq\alpha_m<\pi/2$. The parameter $\alpha_m$ indicates the maximum open angle of the curved detector such that $q(\alpha,\beta)=0$ for $|\alpha|>\alpha_m$. Furthermore, using Eq. (11) and the fact that $p(\xi,\phi)=p(-\xi,\phi+\pi)$, it can readily be show that $$q(\alpha,\beta)=q(-\alpha,\beta+\pi). \qquad (12)$$

A comparison of Eqs. (10) and (12) provide another relationship.

$$p(\xi,\phi)=q(-\alpha,\beta+2\alpha+\pi). \qquad (13)$$

The two relationships in Eqs. (10) and (13) can be employed for estimation of the ideal sinogram $p(\xi,\phi)$ from knowledge of the fan-beam sinogram $q(\alpha,\beta)$ which can be measured in fan-beam CT. Because one can reconstruct $a(r,\theta)$ exactly from full knowledge of $p(\xi,\phi)$, where $\xi\geq 0$ and $0\leq\phi\leq 2\pi$, Eqs. (10) and (13) in fact, provide two mathematically identical estimates of $p(\xi,\phi)$ for $\xi\geq 0$ from knowledge of $q(\alpha,\beta)$ at positive and negative values of $\alpha$, respectively. In practice, however, one can obtain only a finite set of samples of the fan-beam sinogram $q(\alpha,\beta)$. Estimation of $p(\xi,\phi)$ from these samples of $q(\alpha,\beta)$ generally involves 2D interpolations because of the non-linear relationship between the $\{\xi,\phi\}$ and $\{\alpha,\beta\}$ spaces (see Eq. (11)). Accurate 2D interpolations may not only increase considerably the computational load, but also, and more importantly, introduce bias and artifacts into estimates of the ideal sinogram $p(\xi,\phi)$. An alternative approach is proposed that can in effect avoid such 2D interpolations and which can achieve a bias-free variance reduction in the estimated ideal sinogram by using the statistically complementary information inherent in the data of fan-beam CT.

Because $p(\xi,\phi)$ and $q(\alpha,\beta)$ are periodic functions of $\phi$ and $\beta$, respectively, they can be expanded into Fourier series with the expansion coefficients given by $$P_k(\xi) = \frac{1}{2\pi}\int_{\phi=0}^{2\pi} p(\xi,\phi)e^{-jk\phi}d\phi \qquad (14)$$

and $$Q_k(\alpha) = \frac{1}{2\pi}\int_{\beta=\phi}^{2\pi} q(\alpha,\beta)e^{-jk\beta}d\beta \qquad (15)$$

respectively, where the integer k is the angular frequency index. Using Eqs. (10–11) and (13–15), it can readily be show that $$P_k(\xi)=\gamma^k Q_k(\alpha) \qquad (16)$$

and that $$P_k(\xi)=(-1)^k\gamma^{-k}Q_k(-\alpha), \qquad (17)$$

where $\gamma$ is a function of $\alpha$, given by $\gamma=e^{-j\alpha}$.

Equations (16) and (17) provide two relationships between the coefficients of the Fourier series expansions of the ideal and fan-beam sinograms. In the absence of noise and of the effect of finite sampling, for $\xi\geq 0$, Eqs. (16) and (17) provide two mathematically identical estimates of $P_k(\xi)$ (or, equivalently, the ideal sinogram) from knowledge of $Q_k(\alpha)$ (or, equivalently, the fan-beam sinogram) at positive and negative values of $\alpha$. Using Eqs. (16) and (17) for estimating the ideal sinogram from the fan-beam sinogram involves no explicit interpolation between the $\{\phi\}$ and $\{\beta\}$ subspaces.

In the presence of data noise, the measured fan-beam sinogram $q(\alpha,\beta)$ and the coefficient $Q_k(\alpha)$ of its Fourier series expansion can be treated as stochastic processes. (Here and in the following, bold and normal letters denote a stochastic process and its mean, respectively.) Therefore, the outcomes of $Q_k(\alpha)$ and $Q_k(-\alpha)$ may be different due to statistical variations. Consequently, when they are used in Eqs. (16) and (17), the resulting two estimates of $P_k(\xi)$ may be different. This observation implies that $Q_k(\alpha)$ and $Q_k(-\alpha)$ (i.e., the measured fan-beam sinogram) contain statistically complementary information. In order to make use of this information, we first explore the statistical relationship between $Q_k(\alpha)$ and $Q_k(-\alpha)$.

Using Eq. (15), one can express the covariance of as $Q_k(\alpha)$ as $$\text{Cov}\{Q_k(\alpha), Q_k(\alpha')\} = \quad (18)$$
$$\frac{1}{4\pi^2}\int\int_{\beta,\beta'=0}^{2\pi}\text{Cov}\{q(\alpha,\beta),q(\alpha',\beta')\}e^{-jk\beta-k'\beta'}d\beta d\beta',$$

where $\text{Cov}\{q(\alpha,\beta),q(\alpha',\beta')\}$ is the covariance of the data $q(\alpha,\beta)$. Therefore, the covariance between $Q_k(\alpha)$ and $Q_k(-\alpha)$ is given by $$\text{Cov}\{Q_k(\alpha), Q_k(-\alpha)\} = \quad (19)$$
$$\frac{1}{4\pi^2}\int\int_{\beta,\beta=0}^{2\pi}\text{Cov}\{q(\alpha,\beta),q(-\alpha,\beta')\}e^{-jk(\beta-\beta')}d\beta d\beta'$$

and the variances of $Q_k(\alpha)$ and $Q_k(-\alpha)$ are given by $$\tau_{k\pm}^2(\alpha) = \text{Var}\{Q_k(\pm\alpha)\} = \quad (20)$$
$$\frac{1}{4\pi}\int\int_{\beta,\beta=0}^{2\pi}\text{Cov}\{q(\pm\alpha,\beta),q(\pm\alpha',\beta')\}e^{-jk(\beta-\beta')}d\beta d\beta'$$

In an effort to exploit the statistically complementary information inherent in $Q_k(\alpha)$ and $Q_k(-\alpha)$ to reduce variances in the estimates of $P_k(\xi)$, the two estimates provided by Eqs. (16) and (17) are combined linearly to form a final estimate $$P_k^{(w)}(\xi)=\omega(\alpha,k)[\gamma^k Q_k(\alpha)]+(1-\omega(\alpha,k))[(-1)^k\gamma^{-k}Q_k(-\alpha)], \quad (21)$$

where $\xi \geq 0$, $|k|=0, 1, 2, \ldots$, and $\omega(\alpha,k)$ is the combination coefficient that can be a complex function of $\alpha$ and k with a real part $R(\alpha,k)$ and an imaginary part $I(\alpha,k)$. The superscript "$\omega$" indicates that $P_k^{(w)}(\xi)$ is estimated with a combination coefficient $\omega(\alpha,k)$.

Because Eqs. (16) and (17) are mathematically equivalent, the final estimate $P_k^{(w)}(\xi)$ is an unbiased estimate of for any value of $\omega(\alpha,k)$. An image that is reconstructed from $P_k^{(w)}(\xi)$ with a linear algorithm such as the FBP algorithm is also unbiased. The linear in Eq. (21) can be interpreted as a particular estimation method for $P_k^{(w)}(\xi)$ (i.e., the ideal sinogram) because each choice of $\omega(\alpha,k)$ gives rise to a particular final estimate $P_k^{(w)}(\xi)$. Also, because, in principle, $\omega(\alpha,k)$ can have any real and/or complex values, Eq. (21) consists, in effect, of infinite classes of estimation methods. Therefore, the introduction of $\omega(\alpha,k)$ in fact provides an opportunity for a bias-free reduction of the variance of the final estimate $P_k^{(w)}(\xi)$.

Using Eq. (21), one can derive the variance of $P_k^{(w)}(\xi)$, which is given by $$\text{Var}\{P_k^{(w)}(\xi)\}=\tau_{k+}(\alpha)\tau_{k-}(\alpha)\{[t_++t_--2(-1)^k\rho_k^{(r)}(\alpha)](R^2(\alpha,k)+I^2(\alpha,k))-$$
$$[2t_--2(-1)^k\rho_k^{(r)}(\alpha)]R(\alpha,k)-(-1)^k\rho_k^{(i)}(\alpha)I(\alpha,k)+t_-\}, \quad (22)$$

where $t_+=1/t_-=\tau_{k+}(\alpha)/\tau_{k-}(\alpha)$, $\rho_k^{(r)}(\alpha)$ and $\rho_k^{(i)}(\alpha)$ are the real and imaginary parts, respectively, of a correlation coefficient $$\gamma^{2k}\frac{\text{Cov}\{Q_k(\alpha), Q_k(-\alpha)\}}{\tau_{k+}(\alpha)\tau_{k-}(\alpha)}.$$

Minimizing $\text{Var}\{P_k^{(w)}(\xi)\}$ in Eq. (22), one can readily derive optimal $\omega_{op}$ with the real and imaginary parts as $$R_{op}(\alpha,k) = \frac{t_--(-1)^k\rho_k^{(r)}(\alpha)}{t_++t_--2(-1)^k\rho_k^{(r)}(\alpha)} \quad (23)$$

and $$I_{op}(\alpha,k) = \frac{(-1)^k\rho_k^{(i)}(\alpha)}{t_++t_--2(-1)^k\rho_k^{(r)}(\alpha)},$$

respectively. The resulting minimum variance of $P_k^{(w)}(\xi)$ is given by $$\text{Var}\{P_k^{(w)}(\xi)\}_{\min} = \tau_{k+}(\alpha)\tau_{k-}(\alpha)\frac{1-|\rho_k^{(r)}(\alpha)|^2-|\rho_k^{(i)}(\alpha)|^2}{t_++t_--2(-1)^k\rho_k^{(r)}(\alpha)}. \quad (24)$$

It can also be shown that the variance value in Eq. (24) is a true minimum. The dependence of the optimal $\omega_{op}$ in Eq. (23) upon the second-order statistics, such as $\tau_{k+}(\alpha)$, $\tau_{k-}(\alpha)$, $\rho_k^{(r)}(\alpha)$ and $\rho_k^{(i)}(\alpha)$, of the data noise indicates that, for correlated data noise, the optimal $\omega_{op}$ is not, in general, obtainable without prior knowledge of the data noise properties. However, as will be shown below, under certain realistic experimental conditions in fan-beam CT, the optimal $\omega_{op}$ is always an obtainable constant.

The ideal sinogram can be readily obtained from the estimated $P_k^{(w)}(\xi)$ by carrying out the inverse Fourier series expansion and subsequently reconstruct the image by using the computationally efficient and numerically stable FBP algorithm, which is given by $$a(r,\theta) = \int_{\phi=0}^{2\pi}\int_{\xi=0}^{\infty}p^{(\omega)}(\xi,\phi)h(r\cos(\phi-\theta)-\xi)d\xi d\phi \quad (25)$$

where the estimated ideal sinogram is given by $$p^{(\omega)}(\xi,\phi) = \sum_{k=-\infty}^{\infty}P_k^{(w)}(\xi)e^{jk\theta}, \quad (26)$$

and the convolver is given by $$h(r\cos(\phi-\theta)-\xi) = \int_{v=-\infty}^{\infty}|v|e^{j2\pi v(r\cos(\phi-\theta)-\xi)}dv. \quad (27)$$

Because one can estimate $P_k^{(w)}(\xi)$ with a reduced variance relative to either one of the two estimates in Eqs. (26) and (27), the reconstructed image $a(r,\theta)$ will, in general, have a reduced variance. For simplicity, the combination of a particular estimation method and the FBP algorithm will be referred to as a hybrid algorithm. As discussed above, there are infinite classes of estimation methods. Therefore, there are also infinite classes of hybrid algorithms each of which is indexed by the combination coefficient $\omega$. In the absence (or presence) of data noise and of the effect of finite sampling, the hybrid algorithms in these classes produce identical (or different) images.

The widely used FFBP algorithm (an alternative to the above hybrid algorithms) which works directly on the fan-beam sinogram can be expressed as $$a_{FFBP}(r,\theta) = \frac{1}{2}\int_{\beta=0}^{2\pi}\frac{F}{L^2}\int_{\alpha=-\alpha_m}^{\alpha_m}\cos\alpha\, q(\alpha,\beta)\left[\frac{\alpha_0-\alpha}{\sin(\alpha_0-\alpha)}\right]^2 h(\alpha_0-\alpha)d\alpha\, d\beta, \quad (28)$$

where $$L = \{[F+r\sin(\beta-\theta)]^2 + [r\cos(\beta-\theta)]^2\}^{\frac{1}{2}} \text{ and} \quad (29)$$

$$\alpha_0 = \arctan\left[\frac{r\cos(\beta-\theta)}{F+r\sin(\beta-\theta)}\right].$$

It should be noticed that the backprojection step in the FFBP algorithm is distance-dependent because the factor $L^{-2}$ is a function of variables r, θ and β, which renders the conventional FFBP algorithm computationally slower than the FBP algorithm and, by extension, than the hybrid algorithms.

GFFBP algorithms are provided as follows:

$$a_{GFFBP}(r,\theta) = \quad (30)$$
$$\frac{1}{2}\int_{\beta=0}^{2\pi}\frac{F}{L^2}\int_{\alpha=-\alpha_m}^{\alpha_m}\cos\alpha\, q^{(\omega)}(\alpha,\beta)\left[\frac{\alpha_0-\alpha}{\sin(\alpha_0-\alpha)}\right]^2 h(\alpha_0-\alpha)d\alpha\, d\beta,$$

where $$q^{(\omega)}(\alpha,\beta) = \sum_{k=-\infty}^{\infty} 2\omega(\alpha,k)Q_k(\alpha)e^{jk\beta} \quad (31)$$

and ω(α,k) is a combination coefficient function that satisfies the condition $$\omega(\alpha,k)+\omega(-\alpha,k)=1. \quad (32)$$

Because Eq. (31) is the inverse Fourier series expansion of the product of ω(α,k) and $Q_k(\alpha)$ in the angular frequency subspace, $q^{(\omega)}(\alpha,\beta)$ can be interpreted as a convolution in the angular space between q(α,β) and a convolver $f^{(\omega)}(\alpha,\beta)$, which is given by $$f^{(\omega)}(\alpha,\beta) \equiv \sum_{k=-\infty}^{\infty} 2\omega(\alpha,k)e^{jk\beta}. \quad (33)$$

Therefore, the GFFBP algorithms in Eq. (30) has exactly the same form as that for the FFBP algorithm in Eq. (28), except for that q(α,β) in Eq. (28) is replaced by its convolved version $q^{(\omega)}(\alpha,\beta)$.

Each choice of ω(α,k) provides a particular GFFBP algorithm. One can obtain the conventional FFBP algorithm in Eq. (28) by choosing ω(α,k)=½ in Eq. (33). Because ω(α,k) can take any value, Eq. (30) thus provides infinite classes of GFFBP algorithms. In the absence of data noise and of the effect of finite sampling, the GFFBP algorithms in these classes yield mathematically identical images. However, as will be shown below, they generally propagate data noise and the effect of finite sampling differently.

For the purpose of establishing the mathematical relationship between the hybrid and GFFBP algorithms, the fan-beam sinogram can be assumed to not contain any noise or the effect of finite sampling. Therefore, all of the stochastic processes involved may be regarded as deterministic variables. Using Eqs. (21) and (26), Eq. (25) can be rewritten as $$\omega(\alpha,k) = \frac{1}{2}$$

By noticing that α and ξ always have the same sign (see Eq. (11)) and that h(r cos(φ+π-θ)+ξ)=h(r cos(φ-θ)-ξ) (see Eq. (27)), and using Eq. (33), the second term in Eq. (34) can be rewritten as $$\int_{\phi=0}^{2\pi}\int_{\xi=-\infty}^{0}\sum_{k=-\infty}^{\infty}\omega(\alpha,k)Q_k(\alpha)e^{jk(\phi-\alpha)}h(r\cos(\phi-\theta)-\xi)d\xi d\phi. \quad (35)$$

Using Eq. (35) in (34) yields $$a(r,\theta) = \frac{1}{2}\int_{\phi=0}^{2\pi}\int_{\xi=-\infty}^{0} q^{(\omega)}(\alpha,\beta)h(r\cos(\phi-\theta)-\xi)d\xi d\phi, \quad (36)$$

where $q^{(\omega)}(\alpha,\beta)$ is given by Eq. (31). Replacing the variables ξ and φ by α and β, one can re-express Eq. (36) as $$a(r,\theta) = \quad (37)$$
$$\frac{1}{2}\int_{\beta=0}^{2\pi}\frac{F}{L^2}\int_{\alpha=-\alpha_m}^{\alpha_m}\cos\alpha\, q^{(\omega)}(\alpha,\beta)\left[\frac{\alpha_0-\alpha}{\sin(\alpha_0-\alpha)}\right]^2 h(\alpha_0-\alpha)d\alpha\, d\beta,$$

Comparison of Eqs. (30) and (37) suggests that $a_{GFFBP}(r,\theta)=a(r,\theta)$. Therefore, in the absence of noise and the effect of finite sampling, under the condition of Eq. (32), the hybrid algorithm (see Eq. (25)) and the GFFBP algorithms (see Eq. (30)) with the same ω(α,k) are mathematically identical. Each GFFBP algorithm with a particular choice of ω(α,k) hence has a counterpart hybrid algorithm with the same ω(α,k) (or vice versa) For example, the conventional FFBP algorithm has a counterpart hybrid algorithm with ω(α,k)=½.

As shown in Eqs. (19) and (20), for a fan-beam sinogram that contains generally correlated noise, Cov{$Q_k(\alpha),Q_k(-\alpha)$} may not be zero, and $\tau_{k+}(\alpha)$ and $\tau_{k-}(\alpha)$ may be different. However, for medical CT applications in the diagnostic energy range, the normalization number (i.e., the number of x-rays that would be detected in the absence of the absorbing object) is generally (100 to 1000 times) larger than the transmitted numbers (i.e., the number of x-rays that would be detected in the presence of the absorbing object). Additionally, both the normalization and transmitted numbers of x-rays are much larger than unity.

Under these practically realistic conditions, it can be shown that, to a very good approximation, the noise in the measured fan-beam sinogram in a medical CT experiment is uncorrelated, i.e., $$\text{Cov}\{q(\alpha,\beta),q(\alpha',\beta')\} = \frac{1}{n(\alpha,\beta)}\delta(\alpha-\alpha')\delta(\beta-\beta'), \quad (38)$$

where δ(·) denotes the Dirac delta function, and n(α,β) is a quantity that is proportional to the mean count density (i.e., the detected number of x-rays per unit length).

Substitution of Eq. (38) into Eq. (18) yields $$\text{Cov}\{Q_k(\alpha), Q_k(\alpha')\} = \frac{\delta(\alpha - \alpha')}{4\pi^2} \int_{\beta=0}^{2\pi} \frac{1}{n(\alpha, \beta)} d\beta, \quad (39)$$

which implies $Q_k(\alpha)$ and $Q_k(-\alpha)$ are uncorrelated because $$\text{Cov}\{Q_k(\alpha), Q_k(-\alpha)\} = 0. \quad (40)$$

Substituting Eq. (38) in Eq. (20), provides $$\tau_{k+}^2(\alpha) = \frac{\delta(0)}{4\pi^2} \int_{\beta=0}^{2\pi} \frac{1}{n(\alpha, \beta)} d\beta \quad (41)$$

and $$\tau_{k-}^2(\alpha) = \frac{\delta(0)}{4\pi^2} \int_{\beta=0}^{2\pi} \frac{1}{n(-\alpha, \beta)} d\beta,$$

respectively. Because the variance of the count density in the sampled sinogram is inversely related to the bin size, the variances $\tau_{k+}^2(\alpha)$ and $\tau_{k-}^2(\alpha)$ appear to be divergent due to $\delta(0)$ in Eq. (41), if the sinogram is sampled continuously and no smoothing is imposed. However, Eq. (41) can be interpreted meaningfully in practical situations where the sampling is fine, but not infinitesimal, which means that $\delta(0)$ can be eliminated by integrating over the sampling width.

Because $n(\alpha,\beta)$ is the mean count density, one can show, similar to Eq. (12), that $n(\alpha,\beta) = n(-\alpha, \beta + 2\alpha + \pi)$. Using this result in Eq. (41), one obtains $$\tau_{k+}^2(\alpha) = \tau_{k-}^2(\alpha), \quad (42)$$

Also, the noise in CT data is often treated as uncorrelated stationary noise, ie., the covariance of $q(\alpha,\beta)$ satisfies Eq. (38) with $n(\alpha,\beta) = \sigma^{-2}$, where $\sigma$ is a constant and independent of $\alpha$ and $\beta$. Under this condition, the results shown in Eqs. (40) and (42) can also be obtained.

Using the results of substituting Eqs. (40) and (42) in Eqs. (23) and (24), it can readily be show that $$R_{op} = \frac{1}{2} \text{ and } I_{op} = 0,$$

respectively, and that the resulting minimum variance of $P_k(\xi)$ is given by $$\text{Var}\{P_k^{(\omega)}(\xi)\}_{min} = \frac{\tau_{k+}^2(\alpha)}{2} = \frac{\tau_{k-}^2(\alpha)}{2}. \quad (44)$$

The important implication of Eq. (43) is that one can always obtain an unbiased optimal estimate of $P_k(\xi)$ with minimum variance by simply combining knowledge of $Q_k(\alpha)$ at both positive and negative values of $\alpha$ with equal weights of $\frac{1}{2}$ in fan-beam CT.

Although the estimated $P_k^{(w)}(\xi)$ with reduced variance can, in general, lead to a reconstructed image with reduced variance, the relationship between the local image variance and the variance of $P_k^{(w)}(\xi)$ is not theoretically evident. However, one can derive an explicit relationship between the global image variance and the variance of $P_k^{(\omega)}(\xi)$.

For fan-beam CT, Eqs. (21) and (40) can be used to show that, for $\xi$ and and $\xi' \geq 0$, $$\text{Cov}\{P_k^{(\omega)}(\xi), P_k^{(\omega)}(\xi')\} = \text{Var}\{P_k^{(\omega)}(\xi)\}\delta(\xi - \xi'). \quad (45)$$

Using this result and Eqs. (25) and (26), it can be shown that the global image variance is given by $$GVar = \int_{\theta=0}^{2\pi} \int_{r=0}^{\infty} \text{Var}\{a(r, \theta)\} r \, dr \, d\theta \quad (46)$$

$$= \frac{\pi}{2} \sum_{k=-\infty}^{\infty} \int_{\xi=0}^{\infty} \text{Var}\{P_k^{(\omega)}(\xi)\} G_k(\xi) d\xi$$

where $$G_k(\xi) = \int_{r=0}^{\infty} |H_k(r, \xi)|^2 r \, dr$$

and $$H_k(r, \xi) = \int_{\phi'=0}^{2\pi} h(r\cos\phi' - \xi) e^{jk\phi'} d\phi'.$$

should be noticed that the same expression can also be derived for the global image variance obtained with the GFFBP algorithms. Because $G_k(\xi)$ and $\text{Var}\{P_k^{(\omega)}(\xi)\}$ are non-negative, Eq. (46) implies that the estimated $P_k^{(\omega)}(\xi)$ with a reduced variance always leads to a reduced global image variance in the reconstructed image. Furthermore, because $\text{Var}\{a(r,\theta)\}$ is non-negative for all $(r,\theta)$, a lower global image variance suggests, in general, lower local variances in the reconstructed image. In particular, by substituting Eq. (44) into Eq. (46), one can see that the global image variance in the image obtained by using both $Q_k(\alpha)$ and $Q_k(-\alpha)$ with equal weights of $\frac{1}{2}$ is only half of that in the image obtained by use of either $Q_k(\alpha)$ or $Q_k(-\alpha)$ alone. This theoretical prediction can be verified by computer-simulation studies.

$Q_k(\alpha)$ can be readily obtained from the measured fan-beam sinogram $q(\alpha,\beta)$ by performing a fast Fourier transform (FFT) with respect to $\beta$.

Using the chosen $\omega(\alpha,k)$ and the calculated $Q_k(\alpha)$ and $Q_k(-\alpha)$ in Eq. (21), $P_k^{(w)}(\xi)$ can be determined. Due to the non-linear relationship between $\xi$ and $\alpha$ (see Eq. (11)), the desired points $\xi$ (at which $P_k^{(\omega)}(\xi)$ to be calculated) do not coincide, in general, with the value of $\alpha$ at which $Q_k(\alpha)$ and $Q_k(-\alpha)$ are sampled. However, $P_k^{(w)}(\xi)$ can be obtained by interpolation of the right side of Eq. (21) for each desired $\xi$ value. Because the sample density of $Q_k(\alpha)$ (i.e., the fan-beam sinogram $q(\alpha,\beta)$ in the $\{\alpha\}$ subspace) is generally high, a linear interpolation is usually sufficiently accurate and will be used in this work. In fact, according to the Whittaker-Shannon sampling theorem, the fan-beam sinogram must be practically band-limited in the $\{\alpha\}$ subspace so that one can reconstruct an accurate image from a finite set of its samples. Therefore, $Q_k(\alpha)$ is also practically band-limited in the spatial-frequency space of $\alpha$. In order to increase the sampling density of $Q_k(\alpha)$ in the $\{\alpha\}$ subspace, one can, for each k, calculate the discrete Fourier transform (DFT) from the original samples of $Q_k(\alpha)$ in the $\{\alpha\}$ subspace and subsequently zero-pad the calculated DFT. By inversion of the zero-padded DFT, one obtains a set of finer samples of $Q_k(\alpha)$ than the original set. Using these fine samples of $Q_k(\alpha)$, one can again use the linear interpolation technique to obtain $P_k^{(w)}(\xi)$ accurately at a desired value of $\xi$.

One can obtain the estimated ideal sinogram, $P_k^{(w)}(\xi, \phi)$ from the calculated $P_k^{(w)}(\xi)$ by performing the inverse FFT with respect to k and then reconstructing the image from $P_k^{(w)}(\xi, \phi)$ by using the FBP algorithm.

$Q_k(\alpha)$ can be calculated by a process similar to the implementation of the hybrid algorithm above.

The value $q^{(w)}(\alpha,\beta)$ can be determined by first obtaining the products $\{\omega(\alpha,k) Q_k(\alpha)\}$ for all k and $\alpha$. Then, $q^{(w)}(\alpha,\beta)$ may be determined by performing the inverse FFT with respect to k, as shown in Eq. (31).

A set of example images will be reconstructed next. The mathematical forms (see Eqs. (37) and (39)) for the conventional FFBP and GFFBP algorithms are identical except for that they use different input data functions $q(\alpha,\beta)$ and $q^{(w)}(\alpha,\beta)$, respectively. Therefore, one can reconstruct the GFFBP image with the conventional FBPP algorithm by simply using $q^{(w)}(\alpha,\beta)$ to replace $q(\alpha,\beta)$.

Figures 6, 7:
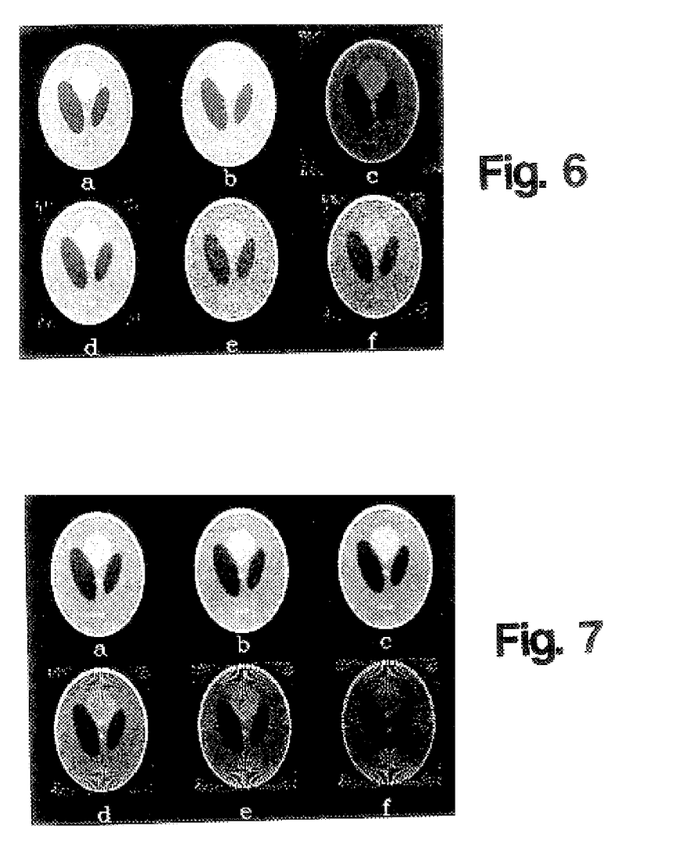
FIG. 6 depicts images reconstructed from the interpolated parallel beam samples of FIG. 5 using an optimal hybrid algorithm and its GFFBP counterpart.
FIG. 7 depicts noiseless images reconstructed from their interpolated parallel beam samples using hybrid algorithms and their GFFBP counterparts.

A numerical Shepp-Logan phantom, represented by a 128×128 array of pixels as shown in FIG. 6a, may be used for the simulation. Using this phantom and an equiangular fan-beam configuration with a focal length F=91 pixels, a noiseless fan-beam sinogram that consists of 128 projections may be generated. These projections are uniformly sampled over 360°, each containing 128 bins that have the same size as that of the image pixels.

In this work, a class of hybrid algorithms were studied and its counterpart class of the GFFBP algorithms that are determined by the following combination coefficient function $$\omega(\alpha, k) = c \quad \alpha > 0 \quad (47)$$
$$= \frac{1}{2} \quad \alpha = 0$$
$$= 1 - c \quad \alpha < 0,$$

where $0 \leq c \leq 1$ is a constant. As shown in Eq. (47), $\omega(\alpha,k)$ is independent of $\alpha$ and k for either $\alpha>0$ or $\alpha<0$ and satisfies Eq. (32). Each value of c determines a hybrid algorithm and its counterpart GFFBP algorithm. Therefore, the parameter c can be used for indexing of the hybrid and GFFBP algorithms in the classes.

By using the noiseless fan-beam sinogram as the mean, 1500 sets of noisy fan-beam sinograms were generated that contain stationary white Gaussian noise. Using a particular hybrid algorithm or a GFFBP algorithm in the classes (see Eq. (47)), 1500 images from these noisy sinograms were reconstructed and empirical variances calculated for the reconstructed images according to $$\operatorname{Var}\{a^{(c)}(\vec{r})\} = \frac{1}{N-1}\left\{\sum_{i=1}^{N}[a_i^{(c)}(\vec{r})]^2 - \frac{1}{N}\left[\sum_{i=1}^{N}a_i^{(c)}(\vec{r})\right]^2\right\}, \quad (48)$$

where N represents the number of reconstructed images (N=1500) in the simulation study; and where $a_i^{(c)}(\vec{r})$ is the value of the image at location $\vec{r}$ reconstructed from the ith set of the noisy sinograms by use of the hybrid (or the GFFBP) algorithm specified by c.

The optimal hybrid algorithm (i.e., c=0.5) and its GFFBP counterpart (i.e., the conventional FFBP algorithm) were used to reconstruct images, which are displayed in FIGS. 6b and 6c, respectively, from the noiseless fan-beam sinogram that consists of 128 projections. The strong artifacts in the outer region of the image in FIG. 6c renders the structure of the Shepp-Logan phantom less visible, indicating that the conventional FFBP algorithm is sensitive to the effect of finite sampling. In order to avoid showing such artifacts in the outer region of the image in FIG. 6c, FIG. 6d is chosen to display only its center portion that contains the phantom. (For the same purpose, below, we will display only the same center portions of images that are reconstructed by use of the GFFBP algorithms with different values of c.) Except for numerical errors in the background of FIG. 6d due to the effect of finite sampling, the images in FIGS. 6b and 6d appear virtually identical, verifying our assertion that, in the absence of noise and the effect of finite sampling, the hybrid and GFFBP algorithms produce identical images. From the corresponding noisy sinogram, we use the same hybrid and GFFBP algorithms to reconstruct images, which are shown in FIGS. 6e and 6f, respectively. Clearly, the two images are different, verifying our assertion that the hybrid and GFFBP algorithms propagate noise differently.

Figure 8:
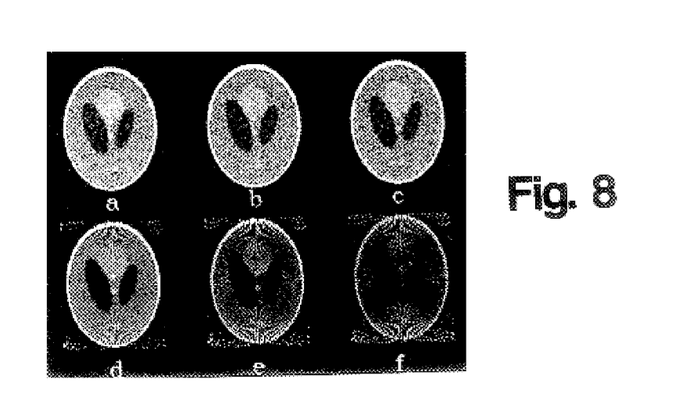
FIG. 8 depicts noisey images reconstructed from their interpolated parallel beam samples using hybrid algorithms and their GFFBP counterparts.

In order to compare the properties of different hybrid and GFFBP algorithms in the classes, the hybrid and GFFBP algorithms (determined with c=0.6, 0.7, and 0.8) were used to reconstruct images from the same noiseless and noisy sinograms used in FIG. 6. FIG. 7 displays the images reconstructed from the noiseless fan-beam sinogram by use of these hybrid (upper row, FIG. 8) and GFFBP (lower row, FIG. 7) algorithms. The images in the upper row are essentially identical except for minor differences due to the effect of finite sampling, again verifying our assertion that the hybrid algorithms with different values of $\omega$ are identical in the absence of noise. However, because the GFFBP algorithms are too sensitive to the effect of finite sampling, the images in the lower row of FIG. 7 appear with different artifacts. Similarly, FIG. 8 display images reconstructed from the noisy fan-beam sinogram by use of the same hybrid (upper row) and GFFBP (lower row) algorithms. The images in the upper row (or in the lower row) in FIG. 8 are obviously different, verifying our theoretical assertion that different hybrid (or GFFBP) algorithms in the classes respond to noise differently.

Figure 9A:
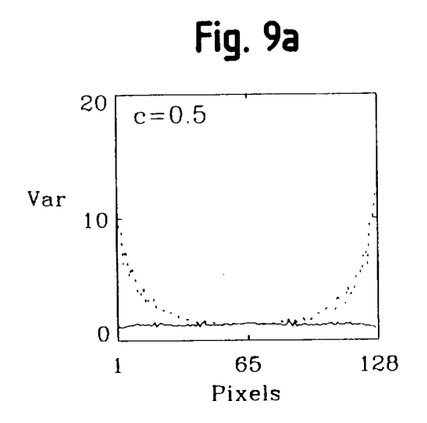
FIGS. 9a and 9b depict imperical image variances obtained from 1500 noisy images.
Figure 9B:
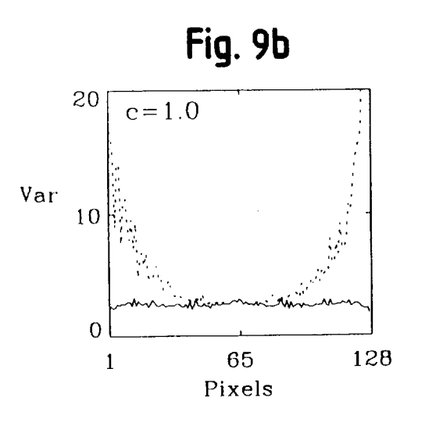

In an attempt to analyze quantitatively the noise properties of the hybrid and GFFBP algorithms, each of 11 hybrid algorithms and their GFFBP counterparts (which are determined with 11 different values of c uniformly distributed between 0 and 1) were used to reconstruct images from 1500 sets of computer generated, statistically independent, noisy fan-beam sinograms. Each of these sinograms consists of 128 projections. Using Eq. (48) one can readily calculate empirically the variance in images reconstructed by using a particular hybrid algorithm (or its GFFBP counterpart). FIG. 9a shows the variances calculated from 1500 images reconstructed by use of the optimal hybrid algorithm determined with c=0.5 (solid curve) and its GFFBP counterpart (dotted curve). Similarly, FIG. 9b displays the variances calculated from 1500 images reconstructed by use of a hybrid algorithm determined with c=1.0 (solid curve) and its GFFBP counterpart (dotted curve). It should be noticed that the variances in FIG. 9b are about twice higher than those in FIG. 9a. This observation is consistent with our theoretical prediction that, for uncorrelated noise, the optimal hybrid algorithm with c=0.5 yields the lowest global image variance.

Figure 10A:
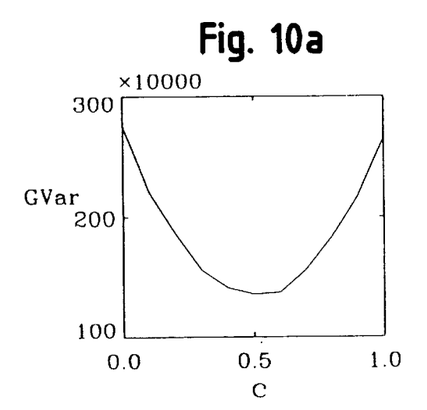
FIGS. 10a and 10b depict global image variances obtained from 1500 noisy images.

Obviously, the image variances depend upon the values of c because the hybrid and GFFBP algorithms studied here are determined by the values of c (see Eq. (47)). From the local image variances obtained with different GFFBP and hybrid algorithms, the global image variances were calculated as functions of c, which are shown as the solid curves in FIGS. 10a and 10b, respectively. For uncorrelated noise, using Eqs. (40), (42), and (47) in (22), one can show that $$GVar \, c^2 - c + \tfrac{1}{2}. \quad (49)$$

Figure 10B:
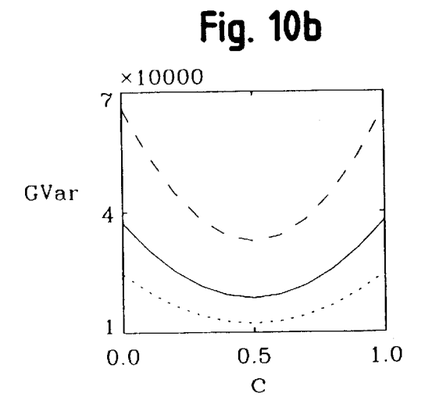

Therefore, GVar is a parabolic function of c, reaching its minimum at $\omega(\alpha,k)=0.5$ (i.e., c=0.5) and its maximum at $\omega(\alpha,k)=0.0$ or $1.0$ (i.e., c=0.0 or 1.0), respectively. The ratio between the maximum and minimum is 2. These predictions are clearly confirmed by the results shown in FIG. 10. The noise properties in the central portions of the reconstructed images were also analyzed, which are typically useful and of interest clinically. The dashed and dotted lines in FIG. 10*b* are the total image variances in the central portions of images reconstructed with the GFFBP and hybrid algorithms, respectively. Clearly, the images reconstructed with the GFFBP algorithms have higher statistical variations than those reconstructed with the hybrid algorithms in these regions.

The proposed hybrid algorithms are combinations of the computationally efficient and numerically stable FBP algorithm and the estimation methods that only involve FFT and simple 1D interpolation operations. On the other hand, the distance-dependent factor $L^{-2}$ in the backprojection step makes the GFFBP algorithm computationally slow. Therefore, the hybrid algorithms have a computational advantage over the GFFBP algorithms, including the conventional FFBP algorithm, In this work, (for the task of reconstructing an image of 128×128 pixels from a fan-beam sinogram that consists of 128 projections by 128 bins) a hybrid algorithm is about 4 times faster than a GFFBP algorithm. Such a computational advantage becomes more significant in reconstruction tasks that involve images and sinograms of large size. For example, clinical CT studies often involve image and sinogram arrays with sizes of 1024×1024 and 1024×1024, respectively.

Both the qualitative (see FIGS. 6–8) and quantitative (see FIGS. 9–10) results above demonstrate clearly that the images reconstructed with the GFFBP algorithms have higher variances (i.e., are noisier) than those reconstructed with the hybrid algorithms, suggesting that the GFFBP algorithms are generally more susceptible to data noise and to the effect of finite sampling than are the hybrid algorithms. This observation can be explained as follows. Under the condition of no image truncation, we have $r \leq F$. Hence, using Eq. (29), one can show that $L^2 = F^2 + r^2 + 2r\eta \leq 2F\eta$, where $\eta = r \sin(\beta-\theta)$ represents the distance from a point $(r,\theta)$ in the image space to the x'-axis, as shown in FIG. 6. Using this result, one obtains $$L^{-2} \geq \frac{1}{2F^2 + 2F\eta} = \frac{1}{2F^2} e^{-ln\left(1+\frac{\eta}{F}\right)}. \tag{50}$$

Since $|\eta,| \leq F$, Eq. (50) can be rewritten as $$L^{-2} \geq \frac{1}{2F^2} e^{-\frac{\eta}{F}}. \tag{51}$$

Clearly, the exponential factor $e^{-\eta/F} > 1$ as $\eta < 0$, and, more importantly, it increases as $\eta$ becomes negatively larger in the outer region of the image space. Therefore, the distance-dependent factor $L^{-2}$ in a GFFBP algorithm amplifies noise and the effect of finite sampling significantly in image reconstruction. This is why the images reconstructed with the GFFBP algorithms, including the FFBP algorithm, are noiser than those reconstructed with hybrid algorithms. This phenomenon was also observed previously in the Tretiak-Metz algorithm for image reconstruction in single-photon emission computed tomography (SPECT) with uniform attenuation.

Because the fan-beam configuration is commonly used for acquisition of projection data, and the conventional FFBP algorithm is used currently for image reconstruction in fan-beam CT, the results of this work may have important implications for image reconstruction in medical CT. As discussed here (and verified with computer-simulation studies), the hybrid algorithms are computationally more efficient and numerically more stable than the GFFBP algorithms, including the conventional FFBP algorithm. Therefore, it appears logically advantageous to adopt the optimal hybrid algorithm (i.e., the hybrid algorithm with $\omega(\alpha,k)=\frac{1}{2}$) for image reconstruction in fan-beam CT.

In this work, the reconstruction and noise properties of images in fan-beam CT was studied. The existence of the statistical complementary information inherent in the projection data was revealed and a linear strategy developed that exploits this information for achieving a bias-free image-variance reduction in fan-beam CT. Based upon this strategy, infinite classes of hybrid and GFFBP algorithms for image reconstruction in fan-beam CT provided. The conventional FFBP algorithm is a special member in classes of the GFFBP algorithms. It has been demonstrated theoretically that, in the absence (or presence) of data noise and of the effect of finite sampling, these hybrid and GFFBP algorithms are identical (or different). The optimal hybrid and GFFBP algorithms were identified theoretically that yield images with the lower global variances among (and hence generally higher SNRs) than other members in their corresponding classes. For uncorrelated data noise that may arise in fan-beam CT, the optimal hybrid algorithm and its GFFBP counterpart, which is the conventional FFBP algorithm, are always obtainable.

Computer-simulation studies were conducted for validation of our theoretical development and for comparison of the computational efficiency and numerical properties between the hybrid and GFFBP algorithms. Extensive numerical results in these studies clearly corroborated the theoretical assertions. These studies suggested strongly that the hybrid algorithms are computationally more efficient than the GFFBP algorithms, including the FFBP algorithm that is currently widely used in fan-beam CT applications. It should be noticed that the computational advantage of the hybrid algorithms becomes even more significant in the applications of spiral CT, which generally reconstruct a large number of fan-beam images of large size. More importantly, the theoretical investigation revealed and quantitative analysis verified that the GFFBP algorithms (including the FFBP algorithm) are more susceptible to data noise and to the effect of finite sampling than the hybrid algorithms. These observations imply that the hybrid algorithms can reconstruct images with generally higher SNRs than do the GFFBP algorithms. Therefore, it may be logically advantageous to use the hybrid algorithms (especially the optimal hybrid algorithm) for image reconstruction in fan-beam CT.

The finite sampling that is employed in both data acquisition and reconstruction unavoidably affects the accuracy as well as the noise characteristics in the reconstructed image. Although the effect of finite sampling was contained in the numerical results of the computer-simulation studies, it is difficult to incorporate this effect into the theory presented in the work. In this work, both hybrid and GFFBP algorithms were investigated in combination with a general combination coefficient $\omega$. However, in the numerical studies, only the noise properties of hybrid and GFFBP algorithms were explored in the classes that are specified by $\omega$ with a form of Eq. (38). One can certainly use other functional forms for $\omega$ and thus can develop other classes of hybrid and GFFBP algorithms. Investigation along this line is certainly worthwhile. Although we focused on discussion of image reconstruction in fan-beam CT, the results can readily be extended to other fan-beam imaging modalities such as fan-beam SPECT with spatially variant focal lengths. In this situation, one needs only replace the relationship (Eq. 11) of CT by that of SPECT (Eq. 6). The theory and method developed for CT are applicable to fan-beam SPECT with constant or spatially variant focal lengths.

A specific embodiment of a method and apparatus for constructing a multidimensional interpolator according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. A method of reconstructing a tomographic image using the parallel beam filtered backprojection algorithm from data, $q(\alpha,\beta)$ acquired with a fan beam configuration with constant or spatially variant focal lengths, such method comprising the steps of:

performing a fast fourier transform on the fan beam data, $q(\alpha,\beta)$, with respect to a set of projection angles, $\beta$;

forming a linear combination of complementary data elements of the transformed data, lying at projection bin $\alpha$ and $-\alpha$;

linearly interpolating the linear combination to obtain a regularly spaced set of data, $P_k^{(\omega)}(\xi)$, in fourier space;

performing an inverse fourier transform on the linearly interpolated data; and reconstructing an image from the inverse transformed data using the filtered back projection algorithm.

2. The method of reconstructing a tomographic image as in claim 1 wherein the step of forming a linear combination of complementary data elements further comprises defining the complementary data elements as two or more data readings obtained from imaging signals passing through the imaged object along a single imaging path.

3. The method of reconstructing a tomographic image as in claim 2 further comprising multiplying the complementary data elements by a combination coefficient.

4. The method of reconstructing a tomographic image as in claim 1 wherein the step of multiplying the complementary data elements by a combination coefficient further comprises multiplying a first element of the complementary data elements by the combination coefficient and a second element of the complementary data elements by a value equal to one minus the combination coefficient.

5. The method of reconstructing a tomographic image as in claim 3 further comprising defining the combination coefficient, $\omega(\alpha,k)$, as a complex number having a real portion $R(\alpha,k)$ and an imaginary portion $I(\alpha,k)$.

6. The method of reconstructing a tomographic image as in claim 1 wherein the step of linearly interpolating the linear combination further comprises selecting a projection angle, $\phi_1$, and an offset distance, $\xi_1$, of a set of regularly spaced data collection points of the regularly spaced set of data.

7. The method of reconstructing a tomographic image as in claim 6 wherein the step of linearly interpolating the linear combination further comprises determining a projection angle, $\beta_1$, of the fan beam data which corresponds to the selected projection angle, $\phi_1$.

8. The method of reconstructing a tomographic image as in claim 7 wherein the step of linearly interpolating the linear combination further comprises determining a set of offset angles, $\alpha_1$, and associated pair of data elements of the fan beam data which correspond to the determined projection angle, $\beta_1$, and the offset distance $\xi_1$.

9. The method of reconstructing a tomographic image as in claim 8 further comprising calculating a pair of fan beam offset distances, $\xi_{fb1}$, $\xi_{fb2}$, for the set of offset angles, $\alpha_1$.

10. The method of reconstructing a tomographic image as in claim 8 further comprising linearly interpolating a data element of the regularly spaced set of data at projection angle $\phi_1$ and offset distance $\xi_1$ based the pair of data elements at offset distances $\xi_{fb1}$ and $\xi_{fb2}$.

11. Apparatus for reconstructing a tomographic image using the parallel beam filtered backprojection algorithm from fan beam data, $q(\alpha,\beta)$, such apparatus comprising:

means for performing a fast fourier transform on the fan beam data, $q(\alpha,\beta)$, with respect to a set of projection angles, $\beta$;

means for forming a linear combination of complementary data elements of the transformed data, lying at projection bins of $\alpha$ and $-\alpha$;

means for linearly interpolating the linear combination to obtain a regularly spaced set of data, $P_k^{(\omega)}(\xi)$, in fourier space;

means for performing an inverse fourier transform on the linearly interpolated data; and means for reconstructing an image from the inverse transformed data using the filtered back projection algorithm.

12. The apparatus for reconstructing a tomographic image as in claim 11 wherein the means for forming a linear combination of complementary data elements further comprises means for defining the complementary data elements as two or more data readings obtained from imaging signals passing through the imaged object along a single imaging path.

13. The apparatus for reconstructing a tomographic image as in claim 12 further comprising means for multiplying the complementary data elements by a combination coefficient.

14. The apparatus for reconstructing a tomographic image as in claim 11 wherein the means for multiplying the complementary data elements by a combination coefficient further comprises means for multiplying a first element of the complementary data elements by the combination coefficient and a second element of the complementary data elements by a value equal to one minus the combination coefficient.

15. The apparatus for reconstructing a tomographic image as in claim 13 further comprising means for defining the combination coefficient, $\omega(\alpha,k)$, as a complex number having a real portion $R(\alpha,k)$ and an imaginary portion $I(\alpha,k)$.

16. The apparatus for reconstructing a tomographic image as in claim 11 wherein the means for linearly interpolating the linear combination further comprises means for selecting a projection angle, $\phi_1$, and an offset distance, $\xi_1$, of a set of regularly spaced data collection points of the regularly spaced set of data.

17. The apparatus for reconstructing a tomographic image as in claim 16 wherein the means for linearly interpolating the linear combination further comprises means for determining a projection angle, $\beta_1$, of the fan beam data which corresponds to the selected projection angle, $\phi_1$.

18. The apparatus for reconstructing a tomographic image as in claim 17 wherein the means for linearly interpolating the linear combination further comprises means for determining a set of offset angles, $\alpha_1$, and associated pair of data elements of the fan beam data which correspond to the determined projection angle, $\beta_1$, and the offset distance $\xi_1$.

19. The apparatus for reconstructing a tomographic image as in claim 18 further comprising means for calculating a pair of fan beam offset distances, $\xi_{fb1}$, $\xi_{fb2}$, for the set of offset angles, $\alpha_1$.

20. The apparatus for reconstructing a tomographic image as in claim 18 further comprising means for linearly interpolating a data element of the regularly spaced set of data at projection angle $\phi_1$ and offset distance $\xi_1$ based the pair of data elements at offset distances $\xi_{fb1}$ and $\xi_{fb2}$.

21. Apparatus for reconstructing a tomographic image using the parallel beam filtered backprojection algorithm from fan beam data, $q(\alpha,\beta)$, such apparatus comprising:

a fourier processor adapted to perform a fast fourier transform on the fan beam data, $q(\alpha,\beta)$, with respect to a set of projection angles, $\beta$;

a combiner processor adapted to form a linear combination of complementary data elements of the transformed data, lying at projection bins of $\alpha$ and $-\alpha$;

a interpolating processor adapted to linearly interpolate the linear combination to obtain a regularly spaced set of data, $P_k^{(w)}(\xi)$, in fourier space;

an inverse fourier processor adapted to perform an inverse fourier transform on the linearly interpolated data; and a reconstruction processor adapted to reconstruct an image from the inverse transformed data using the filtered back projection algorithm.

* * * * *

UNITED STATES PATENT AND TRADEMARK OFFICE
CERTIFICATE OF CORRECTION

PATENT NO.   : 6,115,446
DATED        : September 5, 2000
INVENTOR(S)  : Xiao Chuan Pan Page 1 of 1

It is certified that error appears in the above-identified patent and that said Letters Patent is hereby corrected as shown below:

Column 1,
Line 2, before the heading "Field of the Invention", insert the following heading and paragraph:

STATEMENT REGARDING FEDERALLY
SPONSORED RESEARCH AND DEVELOPMENT

The U.S. Government has a paid-up license in this invention and the right in limited circumstances to require the patent owner to license others on reasonable terms as provided for by the terms of Grant No. R29 CA70449 awarded by the National Institute of Health.

Signed and Sealed this

Sixteenth Day of October, 2001

Attest:

*Attesting Officer*

NICHOLAS P. GODICI
*Acting Director of the United States Patent and Trademark Office*